(12) United States Patent
Rastorgoueff et al.

(10) Patent No.: US 6,792,305 B2
(45) Date of Patent: Sep. 14, 2004

(54) DEVICE AND METHOD FOR TAKING BIOLOGICAL SAMPLE

(75) Inventors: Michel Rastorgoueff, la Celle Saint Cloud (FR); Jean-Philippe Deslys, le Chesnay (FR); Emmanuel Comoy, Saint Aubin (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 130 days.

(21) Appl. No.: 10/168,005

(22) PCT Filed: Dec. 12, 2000

(86) PCT No.: PCT/FR00/03476

§ 371 (c)(1),
(2), (4) Date: Jun. 14, 2002

(87) PCT Pub. No.: WO01/44782

PCT Pub. Date: Jun. 21, 2001

(65) Prior Publication Data

US 2003/0082797 A1 May 1, 2003

(30) Foreign Application Priority Data

Dec. 17, 1999 (FR) .......................................... 99 16018

(51) Int. Cl.⁷ .............................................. A61B 10/00
(52) U.S. Cl. ........................ 600/547; 600/564; 606/167
(58) Field of Search ................................. 600/562, 564, 600/565–567; 606/167, 170; 604/19, 22, 164.01, 164.11

(56) References Cited

U.S. PATENT DOCUMENTS

| 4,116,247 | A |   | 9/1978  | Zanasi                 |
|-----------|---|---|---------|------------------------|
| 4,549,612 | A |   | 10/1985 | Cushing                |
| 5,133,360 | A | * | 7/1992  | Spears ........... 600/567 |
| 5,197,484 | A | * | 3/1993  | Kornberg et al. ... 600/567 |
| 5,423,809 | A |   | 6/1995  | Klicek                 |
| 5,810,806 | A |   | 9/1998  | Ritchart et al.        |
| 5,817,034 | A | * | 10/1998 | Milliman et al. ... 600/566 |
| 5,823,971 | A |   | 10/1998 | Robinson et al.        |
| 6,068,603 | A | * | 5/2000  | Suzuki ............ 600/565 |

FOREIGN PATENT DOCUMENTS

| DE | 94 14 070.7 | 11/1994 |
| WO | WO 97/36160 | 10/1997 |
| WO | WO 99/23950 | 5/1999  |

* cited by examiner

*Primary Examiner*—Charles Marmor
(74) *Attorney, Agent, or Firm*—Merchant & Gould P.C.

(57) ABSTRACT

The invention relates to a device for collecting a soft biological sample and to a method for using the same. The device comprises a hollow cylindrical body (10) with two openings (10A, 10B), one at each end, wherein a piston (12) with a rod (14) is inserted via a first end and the piston-and-rod assembly can be displaced back and forth inside the hollow cylindrically (10), the opening in the second end (10B) of the hollow cylindrical body (10) has a slicing edge (10B) and this second end carries a cutting wire arranged across its opening.

16 Claims, 4 Drawing Sheets

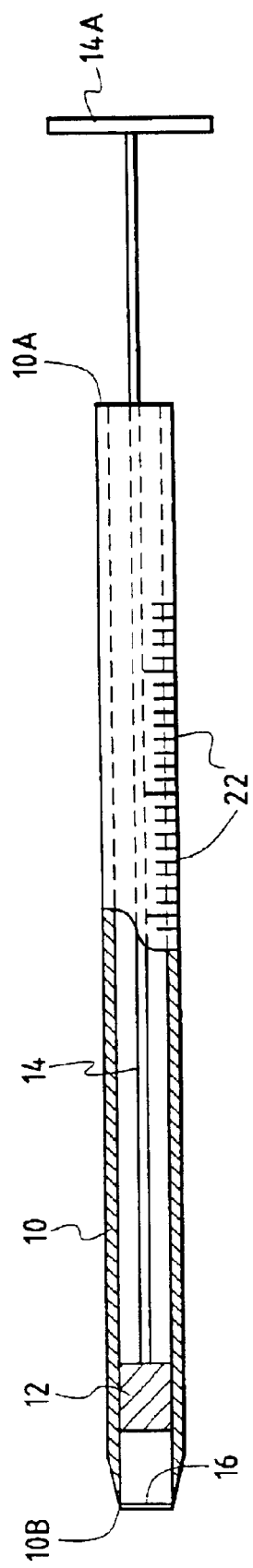
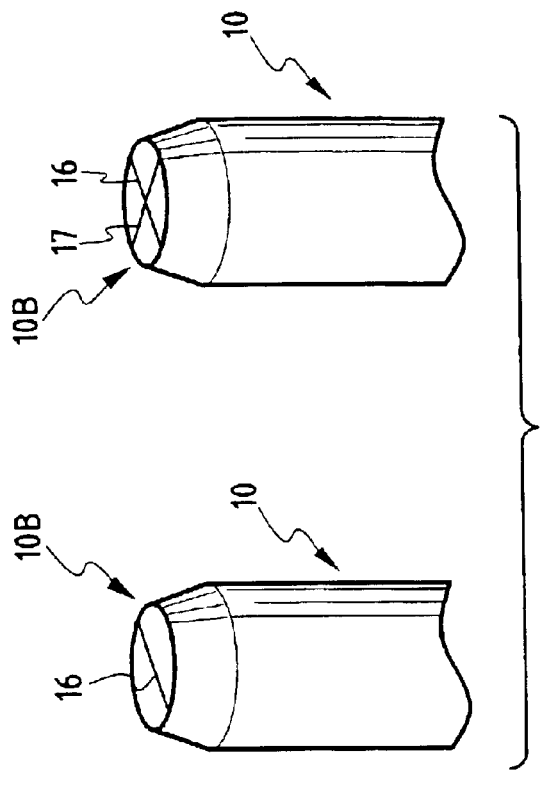
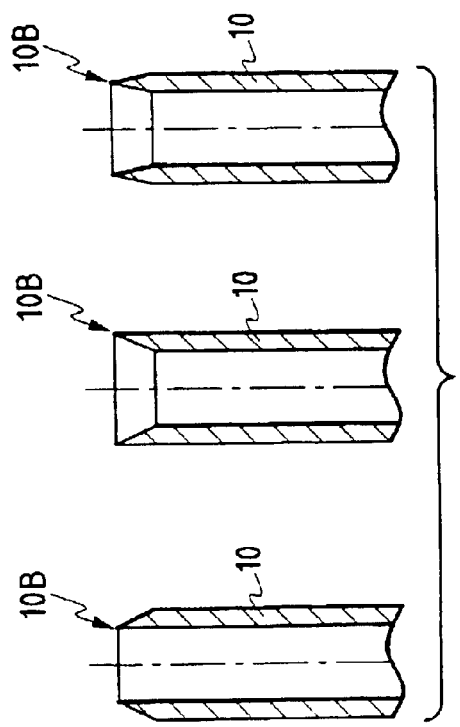

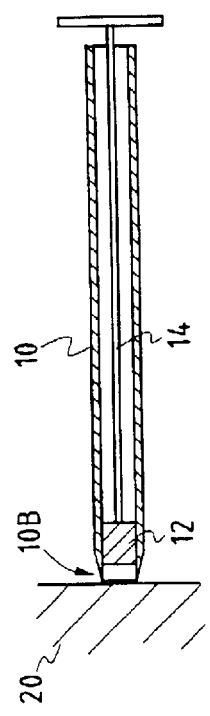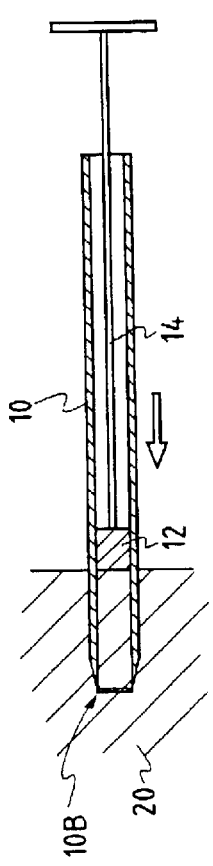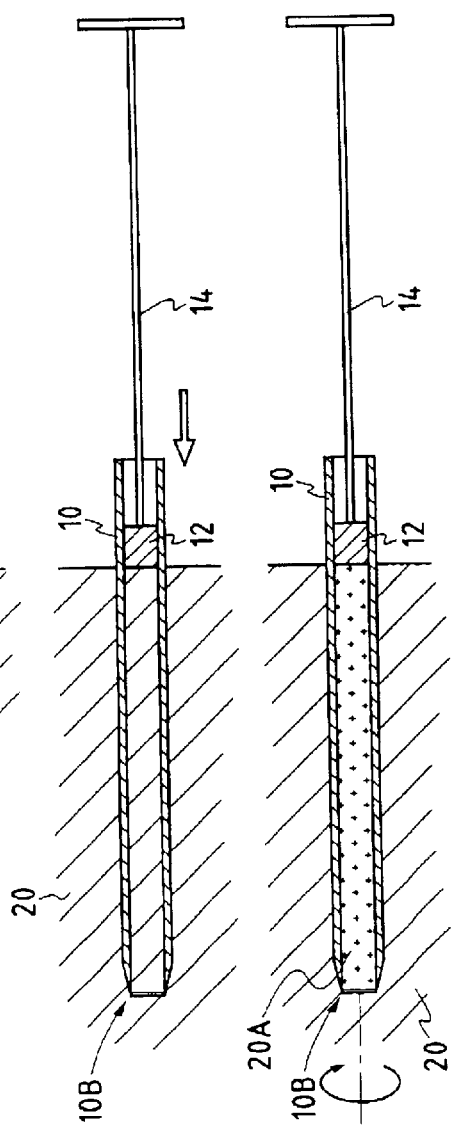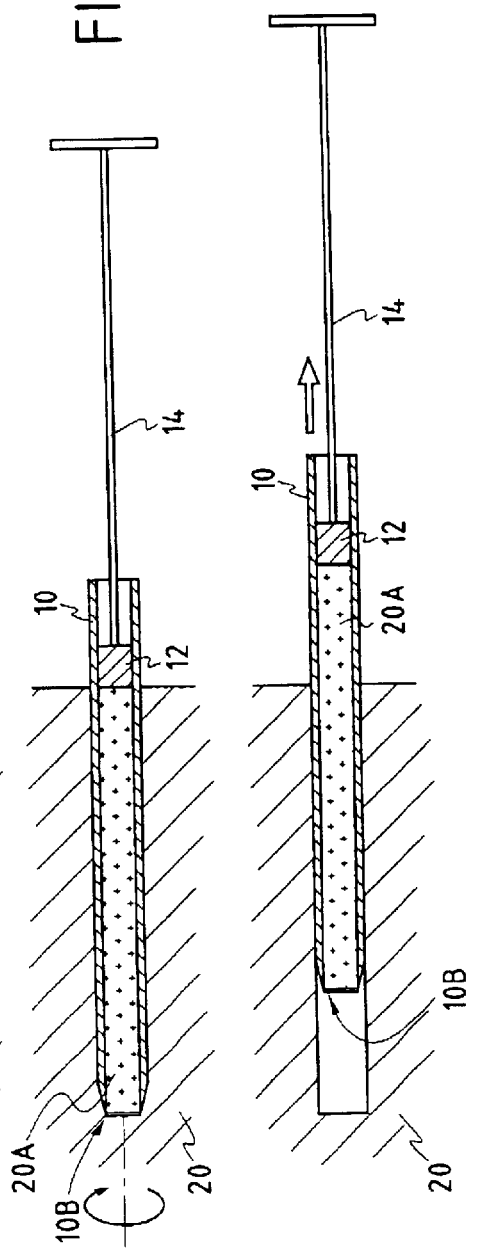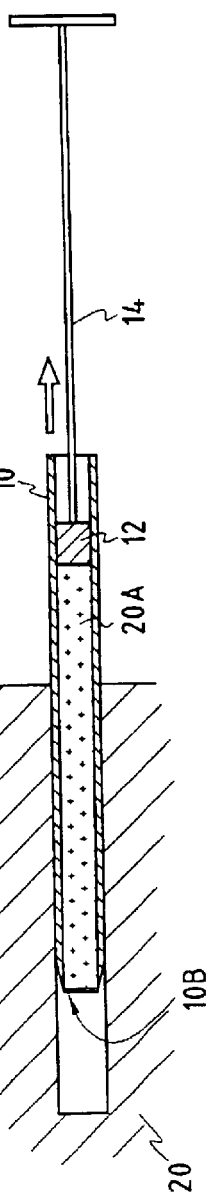
FIG.3A
FIG.3B
FIG.3C
FIG.3D
FIG.3E

DEVICE AND METHOD FOR TAKING BIOLOGICAL SAMPLE

The invention relates to a device for collecting a soft biological sample and to a method of using said device.

BACKGROUND OF THE INVENTION

Biological assays using reagents with a mutual affinity have been known for decades. They involve a biological sample suspected of containing an analyte and one or more reagents with an affinity or ability to react with the analyte in the sample.

The test sample is most frequently a patient's or individual's body fluid such as a sample of whole blood, plasma, serum, urine, cerebrospinal fluid, etc. A sample of biological fluid can be collected simply by using any appropriate device such as a pipette, a syringe, an automatic sample collector, etc. In some cases it may need to be filtered beforehand in order to remove all kinds of unwanted debris or microorganisms. In general terms the methods of sampling body fluids which are performed on a day-to-day basis are satisfactory: they are generally reproducible, giving quantitative results, and the devices available on the market are reliable and relatively inexpensive.

The sample can also consist of a biological solid, such as an organ or tissue fragment, which is not distributed in a systematically homogeneous manner in the sampling device. In this case the method of collecting the sample is much more complex and the devices often have to be adapted to each particular case according to the greater or lesser fluidity or viscosity of these body solids.

A very large number of common analyses and screenings are currently performed on fluid samples. This is not the case of the tests currently performed in the diagnosis of transmissible spongiform encephalopathies (TSE), which are degenerative neurological diseases such as scrapie in sheep, "mad cow disease", also called bovine spongiform encephalopathy (hereafter "BSE"), in cattle, Creutzfeldt-Jakob disease (CJD) and kuru in humans, and related transmissible spongiform encephalopathies.

In the case of BSE, there is not yet a common in vitro diagnostic test which can be performed on a sample of body fluid, but only a test which can be performed on brain samples collected after the animal has been slaughtered. The postmortem examination reveals vacuolations in the cells of the bovine brain tissue and deposits of a specific marker of this disease, namely PrPres (abnormal form of a protein called "prion protein"). Diagnosis currently requires a sample to be collected from the brain matter, especially from the animal's brain stem and more particularly from the sensory and motor nuclei of the vagus nerve, which constitute the zone of preferential accumulation of PrPres, the diagnostic marker of BSE.

The sample collected is then subjected to various treatments for extraction of the PrPres, the specific marker of the disease, which is then analyzed by immunoassay.

The recent incidence of BSE in Great Britain (since 1985), and subsequently in Europe, is the cause of a very considerable public health problem in view of the possibility of transmission of the disease to humans, and its eradication has consequently become of very great economic importance.

In view of its plastic properties and its viscosity, bovine brain matter is not easy to sample in a simple, rapid, reproducible, quantifiable and safe manner. Now, for a mass screening of bovine carcasses, it is essential that the tests—and hence the sampling—are effected in the simplest manner usable in an abattoir, as quickly as possible after slaughter and as reproducibly, quantifiably and safely as possible, i.e. with the best possible sensitivity and without external contamination.

Conventionally, when a sample of brain matter is collected for analysis for the presence of PrPres, it is necessary to use an elaborate protocol which involves cutting off the head, possibly opening the brainpan, seizing a piece of brain matter, for example with a spoon, curette or any appropriate instrument of this kind, and manually cutting off, with a scalpel, at least one portion of said matter until the necessary weight is obtained, which must then be checked with a balance. The scalpel blade has to be changed for each sampling so as to avoid any contamination between samples. This protocol therefore proves rather inconvenient in practice and rather inappropriate for mass screening.

Finally, the sampling operation must be as inexpensive as possible (in terms of equipment and labor) for the final consumer, for obvious reasons.

There is therefore an urgent need for a device for collecting a soft biological sample, particularly brain matter, which is simple, can be used for example in an abattoir or in an analytical laboratory, is quick to use, is economic, has a reproducible performance and is quantifiable, effective and safe from any external contamination. There is also an urgent need for a method of carrying out this type of sampling. The object of the present invention was to meet these needs.

In general, such a need still exists in all situations where it is necessary to collect a soft biological sample, and not only in the area of spongiform disease in cattle or scrapie in sheep.

BRIEF SUMMARY OF THE INVENTION

The inventors have now found that it is possible to collect a reproducible volume of a soft biological sample using a device equipped with a slicing end, making it possible to effect a clean section of the soft matter constituting a sample. In particular, the inventors have discovered that it is possible to collect a constant mass of soft matter using a hollow cylindrical device equipped at one end with a slicing section carrying one or more cutting wires, positioned diametrically and perpendicularly to the axis of said hollow cylindrical body, when said cylindrical device is rotated to a sufficient extent about itself.

"Soft biological sample" is to be understood as meaning a sample of a biological material whose consistency is such that it can be cut effortlessly with a tool such as a scalpel. As indicated previously, an example of such a biological material is brain matter.

"Brain matter" is to be understood as meaning any portion of the mass constituting the central nervous system, and particularly, but not exclusively, the anatomical part conventionally called the "brain stem", especially that which is centered on the sensory and motor nuclei of the vagus nerve, whether said matter be in the natural state or whether it has been treated, e.g. obtained in the form of a pasty ground material.

The invention therefore relates to a device for collecting a soft biological sample, especially of brain matter, comprising a hollow cylindrical body with two openings, one at each end, wherein a piston with a rod is inserted via a first end and said piston-and-rod assembly can be displaced back and forth inside said hollow cylindrical body, characterized in that the opening in the second end of the hollow cylindrical body has a slicing edge and in that said second end carries at least one cutting wire arranged across this opening.

The edge of the second end of the hollow cylindrical body slices sufficiently well to penetrate the soft biological sample by cutting it. The sharpness of the edge may be chosen according to the nature of the sample.

The hollow cylindrical body is advantageously transparent and the piston is advantageously opaque and colored. The hollow cylindrical body and the piston have to be chosen so as to allow and assure substantial leaktightness between them.

The device advantageously has means of identifying a volume corresponding to a variation in the position of the piston in the body. These means comprise e.g. one or more visible marks located in one or more different positions on the hollow cylindrical body and delimiting one or more given cylindrical volumes. Preferably, but not exclusively, the number of visible marks according to the invention is at least two.

The "visible marks" according to the invention, also called identification means, can consist e.g. of conventional graduations, such as those shown in FIG. 1, or of a variety of geometric symbols such as squares, circles, triangles or any symbol of this kind, arranged according to a "pitch" to enable the desired volume to be selected. The word "pitch" is understood here as meaning the distance between two identical marks, for example, but not exclusively, the distance between two identical geometric symbols, namely two triangles, two squares or two circles.

As a variant, the visible marks (at least two) can be located on the rod in at least two different positions in order to define a given cylindrical volume when the rod is displaced by one pitch, i.e. from a first position, in which the first mark coincides with a given zone of the hollow cylindrical body, to a second position, in which the second mark coincides with said zone of the hollow cylindrical body.

Advantageously, the slicing edge of the second end of the hollow cylindrical body is formed by a gradual reduction in the thickness of the wall of this body to give the end a frustoconical shape, or by a chamfer at the end of said body.

Advantageously, the cutting wire is arranged diametrically across the opening in the second end of the hollow cylindrical body and is oriented perpendicularly to the axis of said body.

The steps involved in collecting a soft biological sample using a device according to the invention are as follows:
(1) said device is applied to the surface of said sample, the second end of the hollow cylindrical body being in direct contact with said sample, and the piston-and-rod assembly is then pushed as far as it will go in the forward direction, i.e. towards said second end,
(2) said hollow cylindrical body is pushed into said sample to the desired depth while the piston is kept at the surface of said sample,
(3) when said hollow cylindrical body has reached the desired depth of penetration, said hollow cylindrical body is rotated about its axis to cut the sample by means of at least one cutting wire, and
(4) said hollow cylindrical body and said piston-and-rod assembly, kept as such, are withdrawn from the sample together.

The sample collected may subsequently be extruded from the body of the device, cut and released in order to be dispensed into an appropriate container for detection and/or quantification of the analyte contained in the sample. The sample extrusion and release operations will be described in detail below.

Advantageously, the rotation which enables the wire to cut the sample is performed over 360 degrees.

If the device has the identification means referred to above, these are utilized to identify a sampling volume corresponding to a given penetration of the hollow cylindrical body into the sample and/or to identify a volume extruded from the body of the device for the purpose of analysis.

Thus, if these identification means comprise two visible marks arranged on the hollow cylindrical body, the latter can be pushed into the sample up to a position corresponding to a sampling volume at least equal to the volume given by the mark furthest from the second end of the hollow cylindrical body. An amount given by the displacement of the piston towards the second end of the hollow cylindrical body, between the two marks, can then be kept as the volume for analysis.

If the two visible marks are arranged on the piston rod, the hollow cylindrical body can be pushed into the sample up to a position corresponding to a sampling volume at least equal to the volume given by the mark closest to the end of the rod which carries the piston. An amount given by the displacement of the piston towards the second end of the hollow cylindrical body, between two positions in which this mark and then the other mark successively coincide with a given zone of the hollow cylindrical body, can then be kept as the volume for analysis.

The invention also includes all the variants or combinations which are obvious to those skilled in the art without departing from the spirit of the present invention, for the widest variety of applications in which it is necessary to collect a portion of a soft biological sample.

BRIEF DESCRIPTION OF THE DRAWINGS

The invention will be understood more clearly with the aid of the following Figures, which describe the device and method according to the invention more completely by way of non-limiting examples.

FIG. 1 shows an example of the device according to the invention, partly in longitudinal section and partly as an external view, said device carrying an example of visible graduation marks.

FIGS. 2A and 2B show several variants of the details of the slicing end according to the invention.

FIGS. 3A to 3E illustrate the implementation of the sample collection and extraction method according to the invention.

DETAILED DESCRIPTION OF THE INVENTION

Figure 4A:
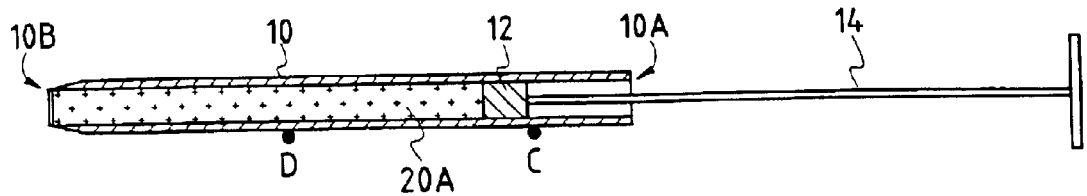
FIGS. 4A and 4B show the use of the device for extruding the desired sample, after it has been collected, according to a pitch defined by the distance between the points C and D.

The device shown in FIG. 1 has a transparent hollow cylindrical body (10) inside which a movable piston (12)

controlled by a rod (14) is fitted, the free end of said rod, opposite the piston, being provided with an actuating head (14A). The piston rod emerges from the tube through the first end (10A) of the latter. The second end (10B) of the tube possesses a slicing edge.

The wall of the tube has a substantially constant thickness over the whole of its length, except in the zone near its second end (10B). In fact, as seen in FIG. 2A, said end can be given a slicing edge by gradually decreasing the thickness of the wall of the tube. This reduction in thickness can give it a frustoconical shape over its outer periphery only, as shown in the left part of FIG. 2A. Said thickness reduction can give it a frustoconical shape over its inner periphery only, as shown in the middle part of FIG. 2A, or form two frustoconical surfaces, over the inner periphery and outer periphery respectively, as shown in the right part of FIG. 2A.

A cutting wire is arranged across the end (10B) of the tube. As shown in the left part of FIG. 2B, this can be a single wire (16) arranged diametrically in the plane of the free end of the end part (10B). As shown in the right part of FIG. 2B, a possible variant is to use two wires (16) and (17) arranged in a cross in the same plane. As a variant forming part of the invention, the perpendicular cutting wire (16) of FIG. 2B can be arranged in the more or less immediate vicinity of the end 10B since it fulfils the cutting function according to the invention.

The wire can be of circular, triangular or other cross-section. In general, any cross-section which is capable of giving the wire a cutting effect when it is displaced in the soft sample material is suitable.

The piston (12) can consist of an attached element mounted on the free end of the rod (14), opposite its actuating head (14A). It can also form a single piece with this rod.

A) Collection of the sample:

FIG. 3A shows the first step of the protocol or implementation of the sample collection method according to the invention. In this first step the device is arranged such that the second end (10B) of the tube is in contact with the soft sample (20) to be collected. At this moment the piston (12) is in its position nearest to this second end.

FIG. 3B shows the next step, which is called core boring, i.e. the gradual rectilinear pushing of the hollow cylindrical body (10) of the device into the soft sample while simultaneously keeping the piston at the surface of the soft sample.

FIG. 3C shows the end of core boring, the hollow cylindrical body (10) having been pushed up to the desired position.

FIG. 3D illustrates the cutting of a portion of the soft sample by rotation of the hollow cylindrical body (10) of the device about its longitudinal axis. The angular amplitude of rotation has to be sufficient for the cutting wire arranged at the end (10B) totally to separate the portion (20A) of sample contained in the hollow cylindrical body (10) from the rest of the soft sample (20). In order to be sure, it will be advantageous to choose an angular amplitude of rotation of 360 degrees or even more.

FIG. 3E shows the collection and extraction of a portion of soft sample from said sample. This step consists in withdrawing the hollow cylindrical tube together with the piston-and-rod assembly, kept as such.

"Kept as such" is understood as meaning that, when the device according to the invention is withdrawn from the sample, the relative positions of the hollow cylindrical body or tube and the piston-and-rod assembly are kept unchanged.

The effect of this step is to extract the "core" or portion of the desired sample.

Figure 6A:
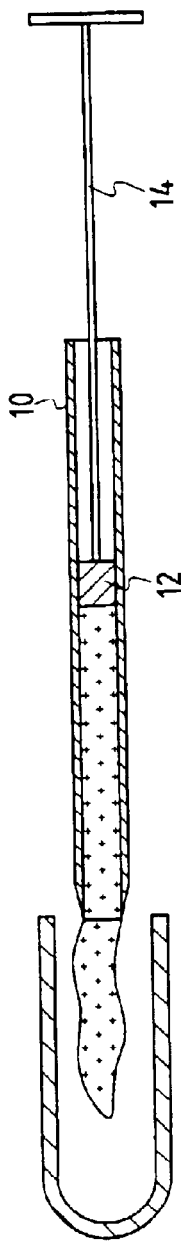
FIGS. 6A, 6B and 6C show the operation of "releasing" the sample into the container by rotating a device according to the invention through 180 degrees and scraping the slicing end 10B against the upper rim of the container.
Figure 6B:
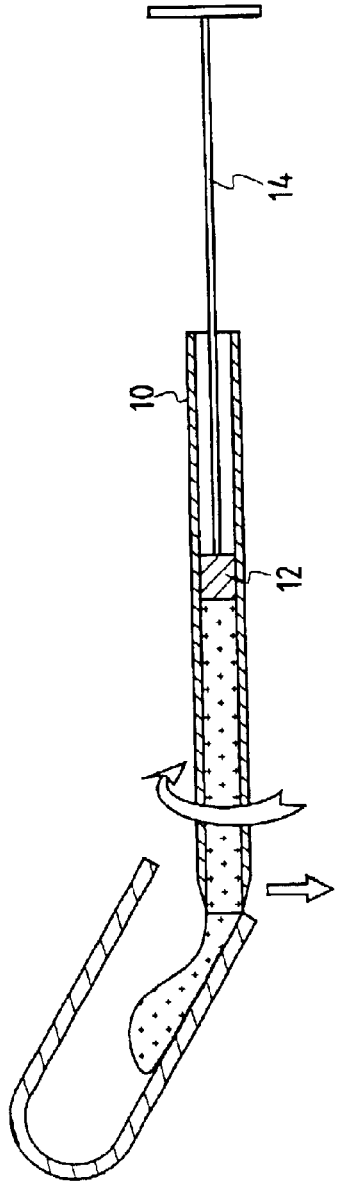
Figure 6C:
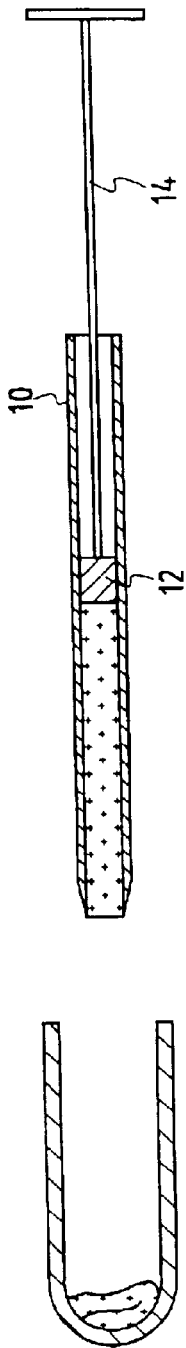

The portion of sample which has now been collected is extruded by expulsion in order to be deposited or dispensed into an appropriate container for subsequent analysis. The extrusion+release step will be described below and is illustrated in FIGS. 6A, 6B and 6C.

In general, in the context of the detection of an analyte, for example a molecule of PrPres, this extruded and released portion of sample is recovered in fine in an appropriate container, known per se to those skilled in the art, for possible extraction of the analyte, as is most frequently the case for a molecule of PrPres.

An essential characteristic of any device according to the invention is the presence of at least one cutting wire at a slicing end of the hollow cylindrical body, said wire being positioned diametrically and perpendicularly to the cross-section of said hollow cylindrical body.

An essential characteristic of any method of collecting a soft biological sample according to the invention is the rotation which is imparted to the hollow cylindrical body in FIG. 3D of the use protocol of the device according to the invention. This is in fact a sufficient rotation of at least 180 degrees which, when a given position—corresponding to a visible or invisible mark—has been reached, is imparted to the hollow cylindrical body and hence to the cutting wire(s), said rotation enabling the clean and reproducible separation of a constant fraction of the sample, irrespective of the consistency of the soft biological material constituting the sample. The effect of said rotation actually transforms the cutting wire(s) into slicing means.

Figure 4B:
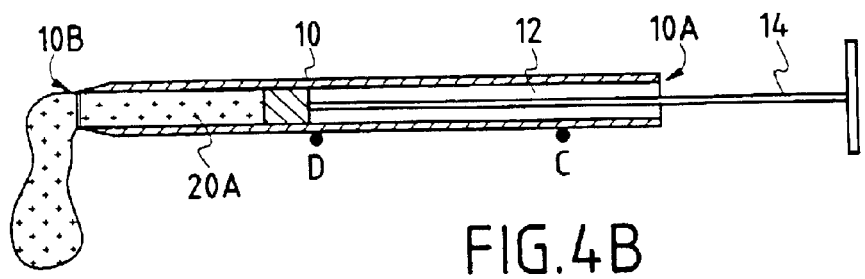

B) Extrusion of the collected sample:

In one particularly advantageous embodiment illustrated in FIGS. 4A and 4B, the device according to the invention comprises a transparent hollow cylindrical body (10) provided with two visible marks, C and D, located between its two ends (10A) and (10B), in two different desired positions delimiting a given cylindrical volume, which in turn makes it possible to define a given mass of soft sample to be collected. This characteristic makes it possible to identify and follow the progress of the piston-and-rod assembly during the extrusion of the collected sample from the transparent hollow cylindrical body. To collect the volume (20A) defined by the marks C and D (cf. FIG. 4A), the piston (12) has been displaced towards the end (10A) at least as far as the mark C furthest from the end (10B). To extrude the collected sample from the transparent hollow cylindrical body (cf. FIG. 4B), it suffices to push the piston (12) in the opposite direction as far as the mark D. Analyses may then be performed on the precise amount of sample delimited by displacement of the piston by one "pitch" from the mark C to the mark D.

Figure 5A:
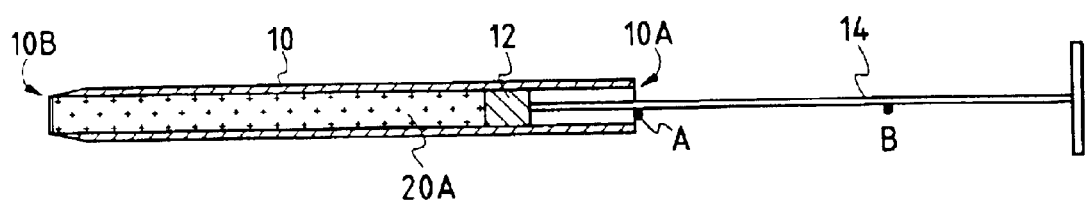
FIGS. 5A and 5B show a variant of FIGS. 4A and 4B in which the desired sample is extruded according to a pitch defined by the distance between the points A and B.

In another particularly advantageous embodiment, the device according to the invention comprises a piston-and-rod assembly of which the rod is provided with two visible marks, A and B, located between its two ends, in two different desired positions defining a given cylindrical volume. This characteristic makes it possible to identify and follow the progress of the piston-and-rod assembly when the collected sample is extruded from the hollow cylindrical body. To collect the volume (20A) defined by the marks A and B (cf. FIG. 5A), the piston (12) has been displaced towards the end (10A) at least until the mark A, which is the nearest to the piston (12), comes into line with a given zone of the transparent hollow cylindrical body (10), which in this case is its first end (10A).

Figure 5B:
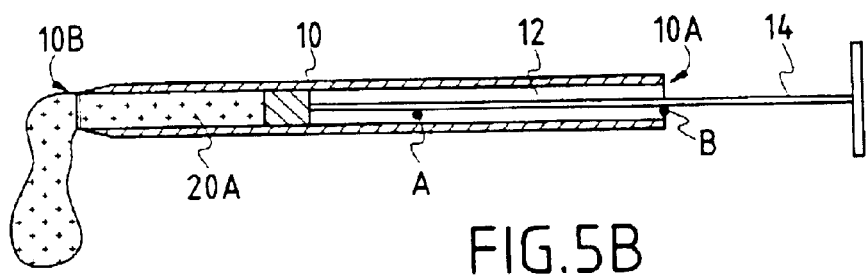

To extrude the collected sample from the transparent hollow cylindrical body (10) (cf. FIG. 5B), it suffices to push the piston (12) in the opposite direction until the mark B comes into line with the end (10A) of the transparent hollow cylindrical body (10). Analyses may then be performed on the amount extruded by displacement of the piston between the position in FIG. 5A and the position in FIG. 5B.

In another particularly advantageous embodiment, the device according to the invention comprises a graduated transparent hollow cylindrical body (10), i.e. a transparent hollow cylindrical body carrying a plurality of graduations over the whole of its length. The graduations make it possible to measure the depth reached in the soft sample by the slicing end of the device, so that the core is cut at exactly the desired level. These graduations are indicated by way of example in FIG. 1, where they are denoted by the reference (22). The graduations also make it possible to identify the displacement of the piston for measuring the volume collected (FIGS. 3A to 3D) as well as for measuring the amount extruded (in a similar manner to that shown in FIGS. 4A and 4B) which will be used for the analyses.

C) Release of the collected sample:

Irrespective of the mode of implementation of the "collection +extrusion" method used above, at the end of the forward movement of the piston (shown in FIG. 4B or 5B) for effecting the desired measured extrusion of the sample, the portion of sample already extruded from the hollow cylindrical body (10) of the device has to be separated from that remaining in said hollow cylindrical body. This can be done in any appropriate manner. Advantageously, it can be done (cf. FIGS. 6A, 6B and 6C) by rotating the device through about 180 degrees while at the same time scraping the slicing end (10B) of the hollow cylindrical body against the upper rim of the container (which can be e.g. a test tube, a flask, etc.) into which it is ultimately desired to release the sample, the container advantageously being inclined by 45 degrees relative to the longitudinal axis of the device so as to facilitate the release of the sample. This has the effect of cutting the sample into two and releasing the extruded portion (this is the so-called sample "release" step). The above rotational movement through about 180 degrees in fact makes it possible to benefit once again from the slicing effect of the wire to improve the quality and reproducibility of the cutting operation and hence of the sample release.

The above-mentioned visible marks and graduations constitute a non-essential feature, albeit one of considerable value to those skilled in the art, for making the collected amounts of sample reproducible, either within one and the same sample or between different samples, at a precise depth which can be determined by the operator in advance, and for making the released amounts of sample reproducible.

The hollow cylindrical body of the device according to the invention can be made of any appropriate solid and impermeable material such as a polymer, like polypropylene, or any other material possessing substantially the same physicochemical characteristics, particularly chemical inertness towards the sample. The transparent hollow cylindrical body of the preferred device is made of polypropylene.

The piston of the device according to the invention can be made of any appropriate solid and impermeable material such as an organic polymer, like silicone, synthetic or natural rubber, polyethylene or polypropylene, or any other material possessing substantially the same physicochemical characteristics, i.e. flexibility (for leaktightness) and chemical inertness towards the sample. The piston of the preferred device is made of polyethylene.

The piston rod of the device according to the invention can be made of any appropriate solid material such as an organic polymer, like polyethylene or polypropylene, or any other material possessing substantially the same physicochemical characteristics. The piston rod of the preferred device is made of polyethylene or polypropylene.

The slicing end carrying at least one cutting wire, the cutting wire and the transparent hollow cylindrical body or tube are made, preferably at the same time, by injection molding of the chosen transparent polymer. An integral mold cavity makes it possible to obtain a functional device at an advantageous cost price.

EXAMPLE 1

Production of Devices According to the Invention

Conventional injection molding, which is known per se to those skilled in the art of plastics, was used to produce several series of polypropylene devices according to the invention, corresponding exactly to FIG. 1 except that the graduations made on the hollow cylindrical body were replaced with visible symbols such as triangles, squares and perpendicular lines, enabling precise volumes to be defined by displacement in the manner shown in FIGS. 4A and 4B. The internal diameter of the hollow cylindrical body was about 0.5 centimeter and its length was about 7.5 centimeters. The distance between two identical symbols (triangles, squares or perpendicular lines) marked on the hollow cylindrical body was about 19.5 millimeters. This distance or "pitch" of about 19.5 millimeters was chosen to ensure that 350 milligrams ±15% of bovine brain stem sample were ejected and released after collection.

A single cutting wire was arranged across the end (10B) of said devices, as shown accurately in the left diagram of FIG. 2B.

EXAMPLE 2

Collection of Bovine Brain Stem

Several series of tests were carried out, showing that the device according to the invention obtained in Example 1 (hereafter called "syringe") enables samples of bovine brain stem to be collected in a very reproducible manner.

First of all, brain stem was collected from different bovines and stored in different plastic bags.

The subsequent protocol of sample "collection+ extrusion+release" was the one described above and illustrated in FIGS. 3A to 3E and FIGS. 4A and 4B; this was followed by release of the sample (FIGS. 6A to 6C) and weighing of the released sample. When the sample was extruded from the syringe, the piston of the syringe was moved forward by one "pitch", for example from one triangle to the next triangle (or from one square to the next square, etc.), spaced 19.5 millimeters apart, in the manner indicated in FIGS. 4A and 4B. The portion of brain stem extruded from the syringe was then cut and released by rotating the device through 180 degrees and simultaneously scraping the sample on the edge of the receiving tube according to the protocol described above (cf. FIGS. 6A, 6B and 6C). The sample was finally weighed on a precision balance sensitive to $\frac{1}{10}$ of a milligram.

Two series of tests were thus carried out using two different batches of syringes.

Series 1 (Results Collated in Table I):

A single experimenter thus performed the brain stem sample "collection+extrusion+release+weighing" operation using 7 different syringes from the same first batch. For this study he repeated this operation several times with each syringe. The total number of tests carried out, taking all the syringes together, was 49.

Table I below summarizes the results obtained.

TABLE I

Measurements (in milligrams) of the samples collected and released using 7 different syringes and a single operator

| Test no. | 1st syringe | 2nd syringe | 3rd syringe | 4th syringe | 5th syringe | 6th syringe | 7th syringe |
|---|---|---|---|---|---|---|---|
| 1 | 343 | 310 | 382 | 320 | 339 | 364 | 361 |
| 2 | 363 | 310 | 358 | 393 | 335 | 330 | 360 |
| 3 | 330 | 334 | 353 | 363 | 328 | 368 | 330 |
| 4 | 358 | 373 | 333 | 310 | 320 | 350 | 366 |
| 5 | 345 | 354 |  | 359 | 342 | 366 | 363 |
| 6 |  | 332 |  | 326 | 353 | 346 | 327 |
| 7 |  | 351 |  | 355 | 329 | 336 |  |
| 8 |  | 352 |  |  | 343 | 369 |  |
| 9 |  |  |  |  | 360 | 356 |  |
| 10 |  |  |  |  | 329 |  |  |
| N = | 5 | 8 | 4 | 7 | 10 | 9 | 6 |
| Mean | 347.80 | 339.50 | 356.50 | 346.57 | 337.80 | 353.89 | 351.17 |
| Standard deviation $\sigma$ | 13.07 | 22.19 | 20.14 | 29.21 | 12.23 | 14.36 | 17.70 |
| CV % = $\sigma$/mean × 100 | 3.76% | 6.54% | 5.65% | 8.43% | 3.62% | 4.06% | 5.04% |

| | | |
|---|---|---|
| TOTAL MEAN | 346.47 | |
| STANDARD DEVIATION | 18.93 | |
| CV % = $\sigma$/mean × 100 | 5.46% | |

The calculated coefficients of variation (denoted by "CV %") in Table I reflect the reproducibility of the brain stem sample "collection+extrusion+release+weighing" operation using the syringe according to the invention.

The inventors found that the results obtained with the syringe according to the invention were remarkably reproducible overall between syringes (CV %=5.46% for n=49 tests). Such a reproducibility is a priori surprising for those skilled in the art, given on the one hand the nature of the raw material and on the other hand the simplicity (crudeness) of the device used.

Series 2 (Results Collated in Table II):

Three operators performed five tests per syringe using a variable number of different syringes originating from a second batch produced according to the procedure of Example 1.

TABLE II

Measurements (in milligrams) of the samples collected and released using different syringes, carried out by 3 operators

| Test no. | 1st syringe | 2nd syringe | 3rd syringe | 4th syringe | 5th syringe | |
|---|---|---|---|---|---|---|
| | | | Operator A | | | |
| 1 | 364 | 334 | 387 | 375 | 320 | |
| 2 | 337 | 361 | 344 | 352 | 323 | |
| 3 | 350 | 359 | 358 | 354 | 387 | |
| 4 | 375 | 300 | 370 | 350 | 364 | |
| 5 | 372 | 349 | 353 | 345 | 376 | TOTAL |
| Mean | 359.6 | 340.6 | 362.4 | 355.2 | 354.0 | 354 |
| Standard deviation $\sigma$ | 15.9 | 25.1 | 16.7 | 11.6 | 30.8 | 20.8 |
| CV % = $\sigma$/mean × 100 | 4.42% | 7.37% | 4.61% | 3.27% | 8.70% | 5.88% |
| | | | Operator B | | | |
| 1 | 337 | 333 | 392 | | | |
| 2 | 382 | 322 | 396 | | | |
| 3 | 332 | 372 | 382 | | | |
| 4 | 362 | 368 | 364 | | | |
| 5 | 344 | 380 | 376 | | | TOTAL |
| Mean | 351.4 | 355.0 | 382.0 | | | 363 |
| Standard deviation $\sigma$ | 20.5 | 25.8 | 12.8 | | | 23.6 |

TABLE II-continued

Measurements (in milligrams) of the samples collected and released using different syringes, carried out by 3 operators

| Test no. | 1st syringe | 2nd syringe | 3rd syringe | 4th syringe | 5th syringe |
|---|---|---|---|---|---|
| CV % = σ/mean × 100 | 5.83% | 7.27% | 3.35% | | 6.50% |
| Operator C | | | | | |
| 1 | 342 | 357 | 393 | | |
| 2 | 365 | 402 | 355 | | |
| 3 | 347 | 338 | 315 | | |
| 4 | 310 | 411 | 343 | | |
| 5 | 369 | 381 | 329 | | TOTAL |
| Mean | 346.6 | 377.8 | 347.0 | | 357 |
| Standard deviation σ | 23.5 | 30.5 | 29.8 | | 30.1 |
| CV % = σ/mean × 100 | 6.78% | 8.07% | 8.59% | | 8.43% |

Overall reproducibility between the tests carried out by operators A, B and C

| | |
|---|---|
| TOTAL MEAN | 357 |
| STANDARD DEVIATION | 24.2 |
| CV % = σ/mean × 100 | 6.78% |

The inventors again found that the results obtained with the syringe according to the invention were remarkably reproducible overall between syringes and between operators (CV %=6.78% for n=55 tests). This reproducibility therefore clearly shows that the syringe according to the invention is simple to operate and easy for anyone skilled in the art to learn.

Therefore, with the syringe according to the invention, it is now easy and justified to avoid weighing the samples for analysis in order to determine whether a sample of brain stem or other brain matter carries PrPres or any other spongiform encephalopathy marker of any type, especially bovine and ovine. The device according to the invention, particularly the syringe, is of general diagnostic application to all these pathological conditions.

The total duration of the sample "collection+extrusion+release" operation is about one minute for an operator who has had some training. It is therefore a particularly rapid operation.

In addition, by virtue of the syringes according to the invention and the plastic bags used, the sample "collection+extrusion+release" operation avoided soiling of the operator's gloves and his environment. This operation is therefore made very clean and is protected from any cross-contamination between samples.

Furthermore, the use of a syringe according to the invention avoids any danger of the operator being cut or pricked and offers safety in terms of the biological risk, which was not the case in the prior art when using a scalpel.

EXAMPLE 3

Collection of a soft vegetable sample:

A series of samples were collected from several bananas using a syringe of the invention obtained according to Example 1.

The syringe made it possible to measure a constant mass of banana easily and reproducibly.

The sample collection experiments were repeated about ten times and the values obtained were extremely similar to one another, confirming once again the reproducibility of use of the syringe according to the invention and hence of the method according to the invention in the collection, extrusion and release of a soft vegetable sample.

The invention described and put into effect in the foregoing Examples therefore makes it possible to obtain a disposable single-use collection device whose use is reproducible, convenient, practical and without danger, and which makes it possible to avoid any contamination between soft samples. The simplicity of the device and its very rapid use make the device and the protocol according to the invention readily suitable for the collection and dispensing, by extrusion and release, of the soft sample, for example of the brain stem type, in an abattoir, an analytical laboratory, etc. The possibility of having devices with graduations and/or visible marks in turn contributes to the necessary excellent reproducibility of sample collection. Finally, the device of the invention can easily be produced industrially according to well-known protocols and in inexpensively.

Of course, the present invention is not limited to the Examples shown, but includes all the variants of the devices and methods according to the invention.

What is claimed is:

1. Device for collecting a soft biological sample, comprising a hollow cylindrical body with two openings, one at each end of said hollow cylindrical body, wherein a piston with a rod is inserted via a first end of said hollow cylindrical body, wherein said piston-and-rod assembly is adapted to be displaced back and forth inside said hollow cylindrical body, the opening in the second end of the hollow cylindrical body has a slicing edge, said second end carries at least one cutting wire arranged diametrically across the opening in the second end of the cylindrical body and is oriented perpendicularly to the axis of said body, and said second end has visible identification means for identifying a volume corresponding to a variation in the position of the piston in the hollow cylindrical body.

2. Device according to claim 1, wherein said hollow cylindrical body is graduated.

3. Device according to claim 1, wherein said hollow cylindrical body is provided with at least two visible identification means located between said two ends of said hollow cylindrical body in two different desired positions delimiting a given cylindrical volume.

4. Device according to claim 3, wherein the visible identification means defines at least one pitch corresponding to a volume of sample to be collected or extruded.

5. Device according to claim 1, wherein the piston is fitted with a rod provided with at least two visible identification means located between the two ends of said rod, in two different desired positions defining a given cylindrical volume.

6. Device according to claim 1, wherein the slicing edge of the second end of the hollow cylindrical body is formed by a gradual reduction in the thickness of the wall of said cylindrical body.

7. Method of collecting a soft biological sample using a device according to claim 1, which comprises the following steps:
   (a) applying said device to the surface of said sample, the second end of the hollow cylindrical body being in direct contact with said sample, and the piston-and-rod assembly is then pushed as far as the piston-and-rod assembly will go tow said second end,
   (b) pushing said hollow cylindrical body into said sample to a desired depth while the piston is kept at the surface of said sample,
   (c) when said hollow cylindrical body has reached the desired depth of penetration, rotating said hollow cylindrical body around an axis of said hollow cylindrical body to cut the sample by means of at least one cutting wire, and
   (d) withdrawing said hollow cylindrical body and said piston-and-rod assembly, kept as such, from the sample together.

8. Method according to claim 7, further comprising the step of:
   (e) extruding and then releasing a desired volume of sample into an appropriate container.

9. Method according to claim 7, further comprising the steps if extruding the collected sample from the hollow cylindrical body of the device and releasing said sample into an appropriate container for at least one of detection and quantification of an analyte contained in the sample.

10. Method according to claim 9 which further comprises the step of using the visible identification means to identify a volume of sample dispensed, extruded and/or released into the container.

11. Method according to claim 7 further comprising the step of using the visible identification means to identify a volume of sample collected, extruded and/or released.

12. Method according to claim 7, further comprising rotating the hollow cylindrical body, to cut the sample by means of at least one cutting wire.

13. Method according to claim 12, wherein the hollow cylindrical body is rotated through 180 degrees.

14. Method of using a device according to claim 1 for collecting a soft sample of animal biological material for detection of a molecule of analyte or diagnostic marker of a transmissible spongiform encephalopathy, comprising the steps of:
   (a) applying said device to a surface of said biological material, the second end of the hollow cylindrical body being in direct contact with said biological material,
   (b) pushing the piston-and-rod assembly as far us it will go towards said second end,
   (c) pushing said hollow cylindrical body into said biological material to a desired depth while the piston is kept at the surface of said biological material,
   (d) when said hollow cylindrical body has reached the desired depth of penetration, rotating said hollow cylindrical body around its axis to cut the biological material by means of at least one cutting wire, and
   (e) withdrawing said hollow cylindrical body and said piston-and-rod assembly, kept as such, from the biological material together.

15. Method according to claim 14, wherein the soft sample is a sample of bovine brain stem.

16. Method according to claim 14, wherein the sample of bovine brain stem is taken from a center of a sensory and motor nuclei of a vagus nerve.

* * * * *